United States Patent
Rinaldi et al.

(10) Patent No.: US 11,346,799 B2
(45) Date of Patent: May 31, 2022

(54) ZERO-POWER WIRELESS CHEMICAL SENSOR FOR AGRICULTURAL PESTS AND DISEASE MONITORING

(71) Applicant: Northeastern University, Boston, MA (US)

(72) Inventors: Matteo Rinaldi, Boston, MA (US); Zhenyun Qian, Boston, MA (US); Vageeswar Rajaram, Boston, MA (US); Sila Deniz Calisgan, Boston, MA (US)

(73) Assignee: Northeastern University, Boston, MA (US)

( * ) Notice: Subject to any disclaimer, the term of this patent is extended or adjusted under 35 U.S.C. 154(b) by 416 days.

(21) Appl. No.: 16/653,938

(22) Filed: Oct. 15, 2019

(65) Prior Publication Data
US 2020/0116694 A1    Apr. 16, 2020

Related U.S. Application Data

(60) Provisional application No. 62/745,147, filed on Oct. 12, 2018, provisional application No. 62/832,709, filed on Apr. 11, 2019.

(51) Int. Cl.
*G01N 27/12* (2006.01)
*G01N 33/00* (2006.01)
(Continued)

(52) U.S. Cl.
CPC ........... *G01N 27/12* (2013.01); *G01N 27/125* (2013.01); *G01N 27/26* (2013.01);
(Continued)

(58) Field of Classification Search
CPC ...... G01N 27/12; G01N 27/125; G01N 27/26; G01N 33/0027; G01N 33/0047;
(Continued)

(56) References Cited

U.S. PATENT DOCUMENTS

| 8,211,586 B2 * | 7/2012 | Nakakubo | G01N 27/16 |
| | | | 429/468 |
| 10,643,810 B2 | 5/2020 | Rinaldi et al. | |

(Continued)

FOREIGN PATENT DOCUMENTS

CN    105973952 A *  9/2016  ............. G01N 27/26

OTHER PUBLICATIONS

Berni, J.A. et al., "Thermal and Narrowband Multispectral Remote Sensing for Vegetation Monitoring From an Unmanned Aerial Vehicle", IEEE Transactions on Geoscience and Remote Sensing, vol. 47, No. 3, Mar. 2009, pp. 722-738.

(Continued)

*Primary Examiner* — Benjamin R Schmitt
(74) *Attorney, Agent, or Firm* — Verrill Dana, LLP

(57) ABSTRACT

An ultra-miniaturized, low-cost, and maintenance-free chemical sensor is capable of continuously monitoring the concentration of specific volatile organic compound (VOC) vapors released from crop plants and green plants under distress from pests or disease. The sensor is based on micromechanical structures and relies on the mechanical actuation induced by the chemical interaction between the VOCs and materials in the microstructure to passively generate a wake-up bit when the concentration of VOCs exceeds a predetermined value. The sensor does not consume power while in standby mode (i.e., when certain VOC vapors are not present), and wirelessly communicates the location of impending outbreaks upon detection of a predetermined concentration of certain VOC vapors.

20 Claims, 9 Drawing Sheets

(51) Int. Cl.
*G01N 27/26* (2006.01)
*G08B 21/12* (2006.01)
(52) U.S. Cl.
CPC ..... *G01N 33/0027* (2013.01); *G01N 33/0047* (2013.01); *G01N 33/0075* (2013.01); *G08B 21/12* (2013.01); *G01N 33/0036* (2013.01); *G01N 33/0098* (2013.01)
(58) Field of Classification Search
CPC .......... G01N 33/0075; G01N 33/0036; G01N 33/0098; G01N 27/226; G08B 21/12
See application file for complete search history.

(56) References Cited

U.S. PATENT DOCUMENTS

| | | |
|---|---|---|
| 2016/0099701 A1 | 4/2016 | Rinaldi et al. |
| 2016/0253595 A1 | 9/2016 | Mathur et al. |
| 2019/0006136 A1 | 1/2019 | Rinaldi et al. |

OTHER PUBLICATIONS

Lin, C. et al., "A novel reflectance-based model for evaluating chlorophyll concentrations of fresh and water-stressed leaves", Biogeosciences, 12, 2015, pp. 49-66.

Rinaldi, M., "Sensing Infrared without Power", DARPA ERI Summit 2018, Poster; <https://eri-summit.darpa.mil/docs/ERIPoster_Applications_N-ZERO_Northeastern.pdf>, p. 1.

Rajaram, V., "A False Alarm-Free Zero-Power Micromechanical Photoswitch", IEEE Sensors, New Delhi, Oct. 28, 2018, pp. 1-4.

Rajaram, V., "Zero-Power Electrically Tunable Micromechanical Photoswitches", IEEE Sensors Journal, vol. 18, No. 19, Oct. 1, 2018, pp. 7833-7841.

Kang, S., et al., "Ultra Narrowband Infrared Absorbers for Omni-Directional and Polarization Insensitive Multi-Spectral Sensing Microsystems", IEEE 19th International Conference on Solid-State Sensors, Actuators and Microsystems (Transducers), Kaohsiung, Taiwan, Jun. 18-22, 2017, pp. 886-889.

Rajaram, V., "MEMS-Based Near-Zero Power Infrared Wireless Sensor Node", 2018 IEEE Micro Electro Mechanical Systems, Belfast, Northern Ireland, UK, Jan. 21-25, 2018, pp. 17-20.

Baller, M.K. et al., "A cantilever array-based artificial nose", Ultramicroscopy, 82, (2000), pp. 1-9.

Grant, O.M. et al., Thermal Imaging to detect spatial and temporal variation in the water status of grapevine (*Vitis vinifera* L.), The Journal of Horticultural Science and Biotechnology, 91.1 (2016): 43-54.

Libelium Smart Agriculture Sensor, Smart Vineyard Lebanon Case Study, www.libelium.com/the-first-smart-vineyard-in-lebanon-chooses-libeliums-technology-to-face-the-climate-change/, Nov. 29, 2017, 13 pgs.

Hassan, M.N. et al., "Green leaf volatiles: biosynthesis, biological functions and their applications in biotechnology", Plant Biotechnology Journal, 13.6, (2015), pp. 727-739.

Fall, R. et al., "Volatile organic compounds emitted after leaf wounding: On-line analysis by proton-transfer-reaction mass spectrometry", Journal of Geophysical Research: Atmospheres, 104. D13, (1999), pp. 15963-15974.

Qian, Z. et al. "Zero-power infrared digitizers based on plasmonically enhanced micromechanical photoswitches" Nature Nanotechnology 12, (2017), pp. 969-973 (Abstract only).

Then, D.A. et al., "A highly sensitive self-oscillating cantilever array for the quantitative and qualitative analysis of organic vapor mixtures." Sensors and Actuators B: Chemical, 117.1 (2006), pp. 1-9 (Abstract only).

\* cited by examiner c)

d)

e)

ZERO-POWER WIRELESS CHEMICAL SENSOR FOR AGRICULTURAL PESTS AND DISEASE MONITORING

BACKGROUND

Monitoring of pests and disease in crop fields is a worldwide challenge in agriculture. Manual inspection and judgement based on an individual's experience is still the primary means for detecting impending outbreaks in many areas, especially in low-income countries. Advanced imaging tools (e.g. hyperspectral cameras [1]) combined with sensor fusion (e.g. humidity, temperature and biological sensors [2]) and sophisticated data processing have been used to increase the accuracy of early-stage detection of pest and disease outbreaks and reduce the labor intensity of conventional pests and disease monitoring. However, due to the high cost of the sensor systems required, such an approach is applicable only to specific agriculture sectors with high return-on-investment rate (e.g., vineyards) in developed countries. Moreover, this type of approach uses conventional unattended sensors which constantly consume power to monitor the environment even when there is no sign of pests or disease. Using this approach involves periodic replacement of batteries, leading to high cost, especially where a dense sensor network is deployed in a large geographic area.

SUMMARY

An aspect of the present technology is a chemical sensor for monitoring a concentration of one or more volatile organic compounds (VOCs) released from a plant under distress from pests or disease. The sensor includes a first cantilever beam having (i) a polymer coating that is exposed to an environment of the sensor and selectively binds to one or more VOCs in said environment, and (ii) a first metal contact disposed at a distal end. The sensor further includes a second beam isolated from said environment by a barrier material. The second is beam configured either as a cantilevered beam or as a fixed beam, and includes a second metal contact disposed at a distal end. The first and second metal contacts are separated by a gap when a concentration of said one or more VOCs in said environment is below a selected threshold. Due to mechanical force in said polymer coating, the first and second metal contacts are in contact when the concentration of said one or more VOCs in said environment are at or above the selected threshold.

Another aspect of the technology is a sensor device for monitoring plants for a disease or pest. The device includes the sensor described above and one or more additional sensors selected from sensors detecting and/or quantifying humidity, wind, air flow, air or water temperature, ethylene, a soil mineral, and soil moisture.

A further aspect of the technology is a system for monitoring plants for a disease or pest. The system includes two or more sensors as described above and/or sensor devices as described above. The system can further include a networking module capable of receiving sensor data from individual sensors or sensor devices of the system, optionally analyzing the data, and transmitting the data or analyzed data to a remote server for storage and/or analysis.

Still another aspect of the technology is a method for monitoring a concentration of one or more VOCs in an environment. The method includes the steps of: (a) providing a sensor, sensor device, or sensor system as described above; (b) placing one or more of said sensors in said environment; and (c) detecting a signal from the sensor when a concentration of the one or more VOCs in the environment reaches or exceeds a selected threshold. In an embodiment of the method, the first beam of the sensor contains a heater, and the method further includes: (d) passing a current through the heater for a first period of time, whereby VOC molecules bound to the polymer are dissipated and the switch is reset into an open configuration; and (e) after a second period of time, repeating steps (a) (c).

DETAILED DESCRIPTION

The present technology provides an ultra-miniaturized, low-cost, and maintenance-free chemical sensor capable of continuously monitoring the concentration of specific volatile organic compound (VOC) vapors released from crop plants and green plants under distress from pests or disease. The sensor is based on micromechanical structures and relies on the mechanical actuation induced by the chemical interaction between the VOCs and materials in the microstructure to passively generate a wake-up bit when the concentration of VOCs exceeds a predetermined value. The sensor does not consume power while in standby mode (i.e., when certain VOC vapors are not present), and wirelessly communicates the location of impending outbreaks upon detection of a predetermined concentration of certain VOC vapors.

Studies have shown that crops with green leaves (e.g., rice, maize, and beans) release VOC vapors such as hexanals, hexanols, and hexyl acetates when they are attacked by pests or disease [3]. The localized concentration of VOCs can go up to several 10s of parts per million (ppm) when a leaf is damaged in multiple spots [4]. The combination of detecting selected different VOCs and their concentrations can act as a signature for a type of pest or disease outbreak and its severity. However, the known correlations between certain VOC concentrations and crop health have not yet been exploited in practice for pests and disease monitoring due to the prohibitive cost of high accuracy VOC measuring devices. Even a regular portable VOC meter with ppm level resolution costs over $200, which makes it impractical for use as a networked sensor node.

Figures 1A, 1B:
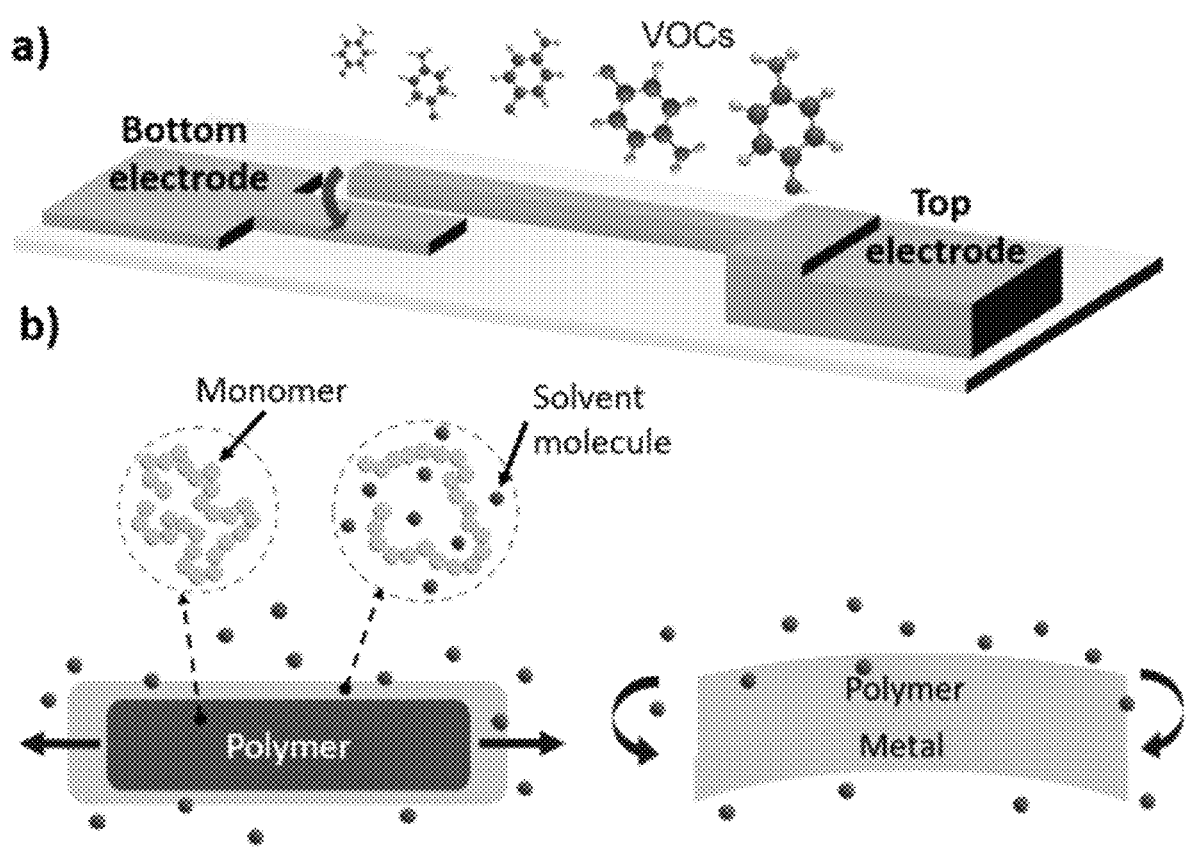
FIG. 1A shows a schematic illustration of the switch of a zero power VOC sensor. The sensor has two electrodes, each containing a layer of conductive material with an air gap between them. The top electrode is coated on its upper surface with a layer of a polymer, which expands upon absorbing the detected VOC compound, thereby closing the contact between the top and bottom electrodes.
FIG. 1B shows a schematic illustration of how expansion of the polymer upon binding the VOC leads to bending of the top electrode to close the contact.

The present technology breaks away from the previous paradigm of using photoionization detectors and active electronics for VOC gas sensing. Instead, the present technology has adapted a zero-power digitizing sensor microsystem technology previously implemented for detecting infrared radiation [5]. As shown in FIG. 1A, the core element of the sensor is a micromechanical switch that is selectively triggered by an above-threshold variation in the local atmospheric vapor level of one or more VOCs or a combination of two or more VOCs of interest. The detected VOCs can be selected as being indicative of the presence of an active plant disease caused by a bacterium, virus, microbe, parasite, insect, arthropod, or a soil condition such as pH, moisture level, or the presence or absence of a soil nutrient, toxin, or metal ion, or another condition of a plant that causes an increase or decrease in release of one or more VOCs from the plant. The switch is triggered by swelling of a polymer layer deposited over the conductive metal layer of one contact caused by selective absorption of the VOC of interest by the polymer. See FIG. 1B.

Figures 2A, 2B, 2C:
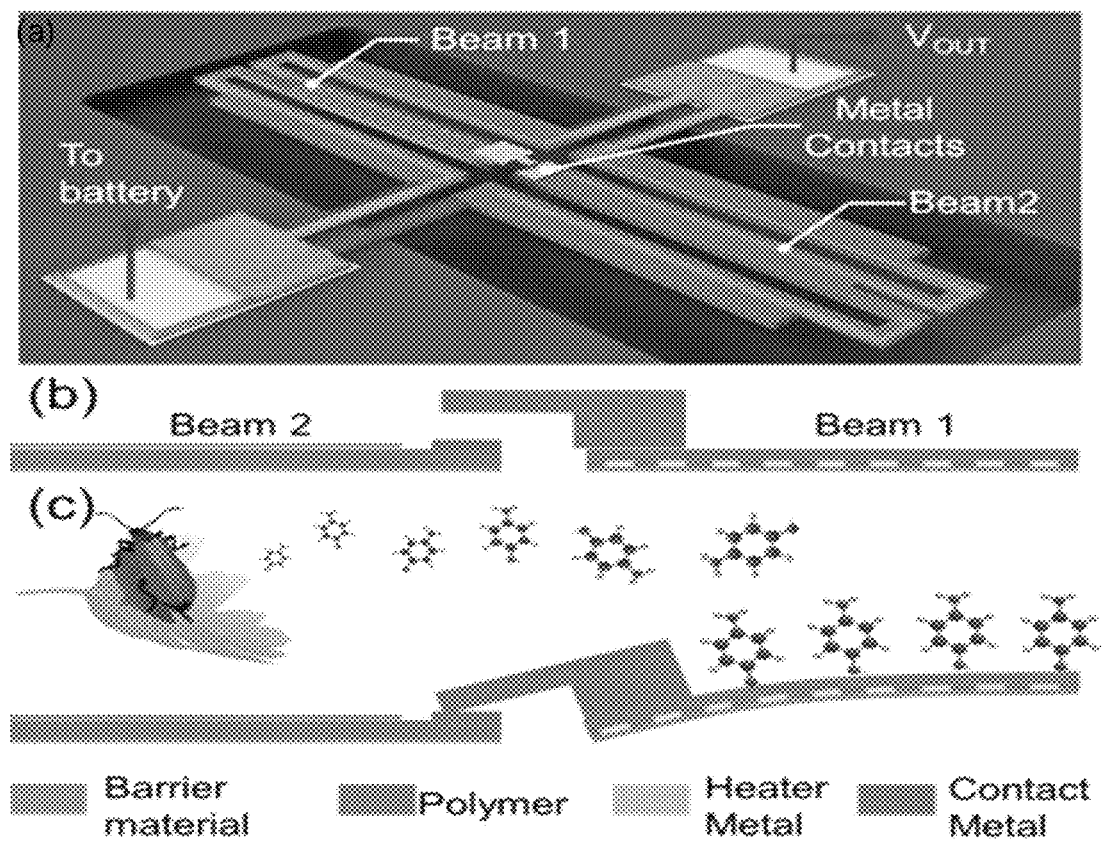
FIG. 2A shows a 3D schematic illustration of a zero power VOC sensor.
FIG. 2B shows a cross section of the central cantilever beams in their standby position.
FIG. 2C shows the beams after target VOC is detected, which triggers the switch when the concentration is higher than a designed threshold value.

The switch can include a symmetric pair of structurally similar beams, one of which is a cantilever beam and the other of which can be cantilevered or fixed (FIG. 2A). One beam (Beam 1, first beam) is exposed to the environment, which may contain VOCs that can contact the polymer layer of the beam. The other beam (Beam 2, second beam) and the rest of the structure is desensitized to the environment by the presence of a thin barrier material, such as a metal, metal oxide, or a polymer which does not bind the VOC of interest. The overall structure of the sensor device including the cantilever beams can be similar to the device described in US2017 0331450, for example (incorporated by reference herein) with the addition of a polymer coating chosen for its ability to bind one or more selected VOCs. When VOC molecules released into the atmosphere, water, or soil by a plant under distress reach the switch (FIG. 2B), an exposed polymer in Beam 1 binds to specific, selected VOCs of interest, causing a net change in the mechanical stress along the thickness of the polymer layer of Beam 1. While Beam 2 can contain the same polymer, or a different polymer, it is covered with a thin layer of a barrier material that prevents contact between the polymer and the VOC of interest; thus, Beam 2 does not bend or otherwise change its shape when exposed to the VOC. Polymers that selectively bind VOCs are known in the art and can be selected from those disclosed in [6], for example. Binding of the VOC of interest to the polymer layer of Beam 1 results in Beam 1 bending downwards due to the stress gradient created between the top and bottom surfaces of the polymer layer. When the VOC concentration reaches the designed threshold, Beam 1 bends down sufficiently to make the two metal contacts on either head touch, which completes an electrical path across the switch (FIG. 2C). Closing of the switch generates a wake-up bit to trigger load electronics, such as a battery-operated wireless transmitter or a wired transmitter. The wireless chemical sensor drains power from the battery, which is preferably degradable in the environment of use, and also can be recharged over time using, for example, a solar panel attached to the sensor device. Only upon detection of one or more targeted VOCs above a predetermined alarm concentration threshold will the switch close and the sensor device transmit a radio frequency signal indicating the presence of pests or disease, or a predetermined level thereof, at the sensor location. At other times, such as at standby, the power consumption is essentially zero (10 nW or less in standby mode), thanks to the physical air gap that separates the switch contacts.

The switch described herein can optionally include a low-power microheater integrated on the bottom of Beam 1 to vaporize the adsorbed VOC molecules after a detection. This re-activates the polymer for further detections and thus resets the switch to its open state. The standby power consumption returns to zero in this case, since a short voltage pulse for heater reset is required only after a detection. The symmetric folded structure prevents false alarms arising from changes in contact gap (which sets the threshold) due to ambient temperature changes and residual stress from fabrication. False alarm rate is expected to be less than 1/day. Packaging solutions similar to the ones used for MEMS microphones may be used to provide mechanical protection to the sensors while exposing it to the surrounding atmosphere. The ultra-miniaturized wireless sensor may be easily retrofitted to fit the deployment requirement of different types of crops. The sensor may be deployed close to plants (for example, within <1 meter of one or more plants, in soil, on top of the soil surface, on or near roots, or on or near leaves, or on a support structure above the ground) in crop fields with a fine spatial granularity. Due to the complete elimination of standby power consumption, the sensor has the ability to wirelessly reveal at least 100, or at least 1000, or several thousands of pest or disease events without replacement of the sensor battery. Thus, the useful lifetime of the sensor is up to about 10 years or more, limited only by the battery self-discharge rate.

Different plant diseases and pests affect plants differently, including affecting different parts of the plant and its sub-structures, leading to the release of different combinations of VOCs, each of which can act as a unique signature of the disease or the pest. By combining multiple switches with various thresholds, each targeting a different VOC, a network of passive logical functions can be realized that can be tuned to respond to specific diseases or pests. False alarm rate is greatly reduced in such implementation, since other sources of VOCs such as fertilizers and pesticides would have different signatures. In the network, each sensor is equipped with a low-power, long-range wireless transmitter that can communicate with a centrally located transceiver, which can be part of an existing cell service infrastructure. The latter collects and processes data from the sensors within its range and then informs end users wirelessly to provide early detection of a pest and/or disease outbreak, or a change in the status of a known pest infestation or plant disease condition The unique features of the sensor include the following. (i) The sensor monitors crops for pest and disease attacks without using any electrical power. (ii) The sensor is capable of continuously and passively monitoring crops for pest or disease-induced distress and wakes up an electronic circuit upon detection of one or more pre-programmed indicators when they exceed threshold values. (iii) The zero-power VOC sensor leverages the structural deformation caused by chemical interaction between one or more selected VOCs and one or more sensor materials to digitize the above-threshold VOC concentration change in the vicinity of the sensor. (iv) The sensor uses a normally-open micromechanical switch with a VOC-sensitive structural material that, on absorbing specific VOCs, changes its mechanical stress, causing it to bend down and close its contacts when exposed to an above-threshold concentration of VOCs. (v) The VOC-sensitive material is engineered to have high chemical specificity to reduce false alarm rate. (vi) In some embodiments, the sensor incorporates a microheater under the VOC-sensitive material to heat up and desorb the VOC molecules after detection to effectively reset it for future detections.

The sensor described herein has several advantages. (i) The sensor consumes no electrical power to check the plants for pest or disease exposure, requires no manual inspection or intervention, and is inexpensive. The zero-power wireless sensor described herein exploits only the energy from the chemical bonds formed between the VOCs released from distressed plants and the sensing material to detect the VOCs, resulting in greatly extended sensor lifetime, up to several years without requiring battery replacement. (ii) The footprint of the sensor node described herein (nanometer range (10-999 nm) or micrometer range (1-999 micrometers) or millimeter range (1-10 mm) is much smaller than that of existing sensors (e.g., palm size) due to the sensor being miniaturized and elimination of large power supplies. (iii) Since battery replacement costs are eliminated, these sensors enable low-cost, maintenance-free, high spatial granularity networks. The scaling in size also directly leads to easier installation and less impedance to farming activities.

The sensors described herein have many applications. These include: (i) development of low-cost agricultural sensor networks for pest and disease monitoring of crops; (ii) development of fully automated response systems (e.g., for fumigation) and alert systems that quickly contain the spread of the pests or disease to minimize their impact on yield (high spatial granularity allows localized response, which in turn reduces the overall resources required to contain the outbreak); and (iii) development of chemical sensors for industries other than agriculture, such as food production and pharmaceutical production.

An ultra-miniaturized (e.g., coin size) and low-cost chemical sensor is capable of continuously monitoring the environment for traces of stress-induced plant-based volatile organic chemicals (VOCs) without consuming any power in standby (i.e., when the plant is not under biotic stress). Such a sensor can be interfaced with a commercial off-the-shelf wireless transmitter that wirelessly communicates relevant information (such as its location) upon the detection of VOCs associated with pest and disease attacks.

The core element of the sensor is a micromechanical beam that includes or consists of a metal layer and a polymer layer, which can be pure, copolymer, or a mixture of two or more different polymers. The polymer is chosen such that its affinity to one or more VOCs of interest is high. In the absence of the relevant VOC(s), interactions between monomers and solvent molecules are more favorable than monomer-monomer interactions. When the sensor is exposed to detectable VOC vapor, the polymer chains can interact with the VOC molecules (which are small compared to the polymer chains) causing an expansion in volume. This swelling effect is exploited as the actuation mechanism for out-of-plane displacement in the proposed switch-based chemical sensor (FIG. 1B). A bi-material design with a polymer layer deposited onto a metal layer is used in order to create an out-of-plane displacement upon absorption or adsorption of VOC molecules by the polymer: while the polymer swells, the metal remains unaffected, causing the bi-material beam to bend down (FIG. 2C). In order to make an effective and highly sensitive sensor, the volumetric expansion of polymer layer can be maximized in response to specific VOC molecules of interest. The affinity of the polymer for a given VOC compound, compared to its intramolecular monomer-monomer interactions to the targeted VOC molecules, can be optimized (made as high as possible) so as to maximize volumetric expansion. Thus, the polymer is chosen such that it has a high affinity towards VOCs whose detection is desired, such as VOCs that are typically released by plants when they are attacked by pests and disease, including hexanals, hexanols (3-cishexan-1-ol), hexyl acetates, toluene, salicylic acid, and estragole. Polymers that can be used to selectively bind VOCs from plants include polymethyl-methacrylate (PMMA), polydimethylsiloxane (PDMS), polystyrene (PS), polyurethane (PU), polyvinylpyrrolidone (PVP), polyether-urethane (PEUT) and their mixtures. PDMS and PEUT have a high affinity for toluene [7] and can be used to detect toluene as VOC.

Figures 3A, 3B, 3C:
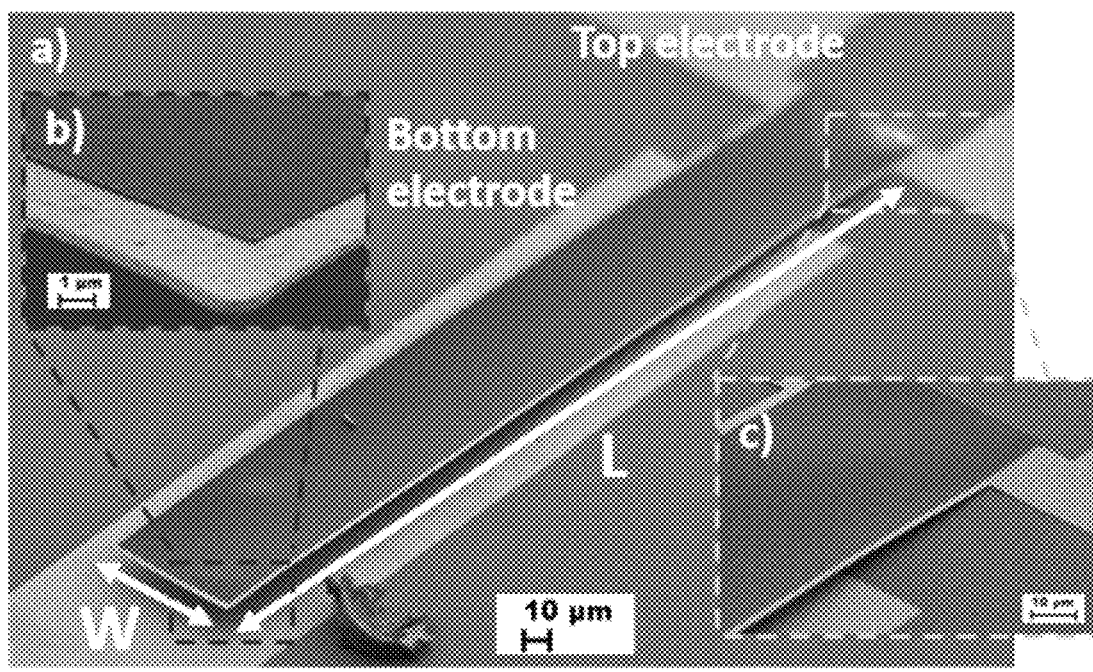
FIG. 3A shows a scanning electron microscope (SEM) image of a micromechanical switch after release with width and length of 60 µm and 400 µm, respectively.
FIG. 3B shows the material stack of the cantilever.
FIG. 3C shows the air gap between the top and bottom electrodes at the contact.
Figures 4A, 4B, 4C, 4D, 4E, 4F:
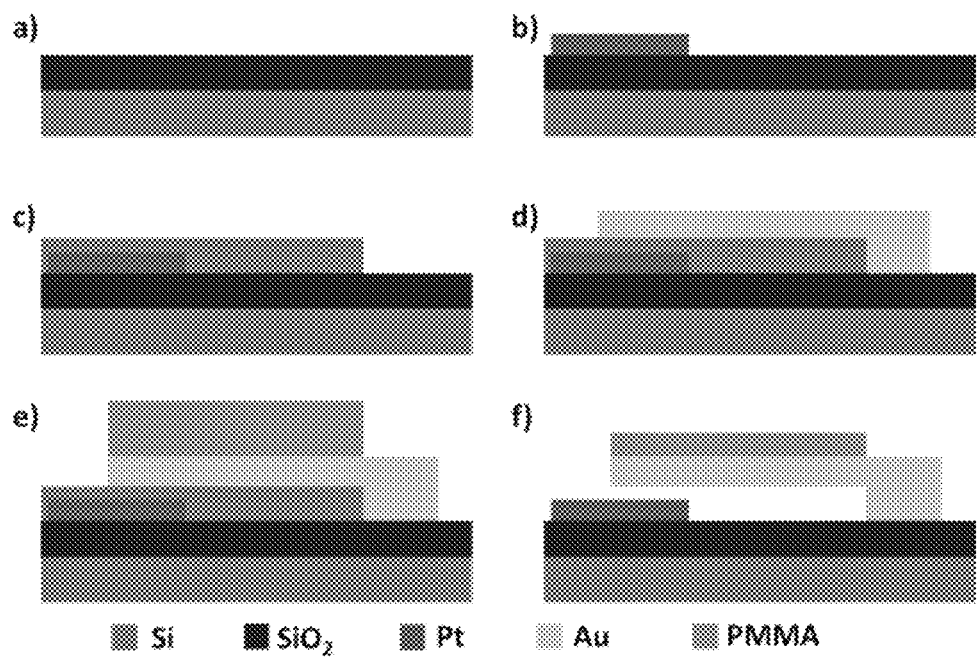
FIGS. 4A-4F show a schematic representation of a 4-mask microfabrication process.

The present technology includes a method of fabricating a zero power VOC sensor. A diagram of an embodiment of the method is shown in FIGS. 4A-4F, depicting a 4-mask microfabrication process. Each layer is patterned by photolithography. FIG. 4A shows deposition of $SiO_2$ by LPCVD. In FIG. 4B, deposition and lift off for the bottom Pt electrode are performed. FIG. 4C shows amorphous deposition of Si and etching for its use as a sacrificial layer. FIG. 4D shows deposition and lift-off of an Au layer for the top electrode. In FIG. 4E, a layer of PMMA polymer is deposited by spin coating. Finally, in FIG. 4F the thinning of the PMMA layer and removal of the Si sacrificial layer by $XeF_2$ are shown. FIGS. 3A-3C show SEMs of a sensor contact fabricated according to this method.

Figure 5:
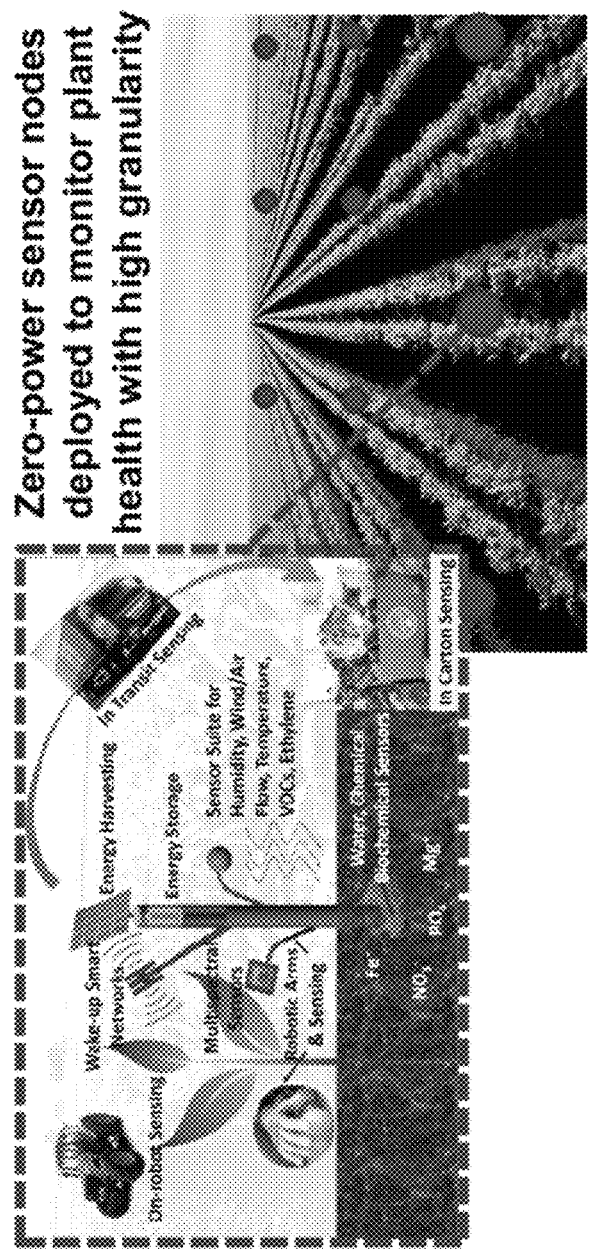
FIG. 5 shows a schematic representation of a system for crop monitoring. Multiple zero power VOC sensors can be distributed throughout a field of crop plants, mounted on a robotic vehicle, or mounted on packaging for harvested plants or crops. The inset shows a single sensor device that includes a VOC sensor and a transmitter for waking up a network when one or more selected VOCs are detected. The sensor device optionally can also include sensors for any combination of humidity, wind, air flow, temperature, and ethylene, configured as a sensor suite. The sensor device can optionally include sensors for soil components such as iron, nitrate, phosphate, Mg, and any combination thereof. The sensor device can optionally include one or more multispectral sensors for airborne compounds, and also can optionally include a module for collecting and storing solar energy.

FIG. 5 depicts a system for the monitoring of plant health. The system includes a deployed array of VOC sensors of the present technology in a field of green leaved plants or crop plants. Each sensor or sensor device can include additional sensors as shown, such as sensors for humidity, air or soil temperature, wind, local air flow, and ethylene (trigger of fruit ripening), as well as IR sensors, optionally multispectral for the more precise analysis of VOCs or other chemicals, a transmitter or transceiver for network communication, as well as an optional solar array for energy harvesting and battery for storage. Sensors, sensor devices, or sensor systems of the present technology can also be deployed by mounting them on robotic devices capable of roaming a field of plants or on cartons for shipping, storage, or sale of crops or plants.

Figures 6A, 6B:
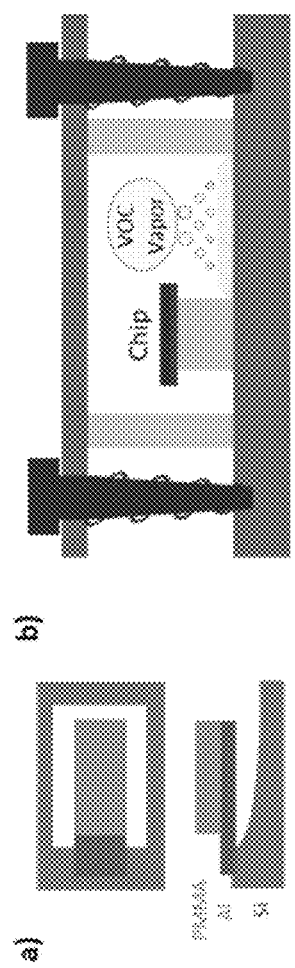
FIG. 6A shows top and side views of the cantilever portion of a prototype zero power VOC sensor after release (to enable vertical displacement), where the cantilever length is 500 µm, width is 60 µm, and a 650 nm thick layer of PMMA is spin-coated on top of a 100 nm thick layer of Al.
FIG. 6B shows the measurement setup used to demonstrate the detection of ethanol as VOC.
Figure 6C:
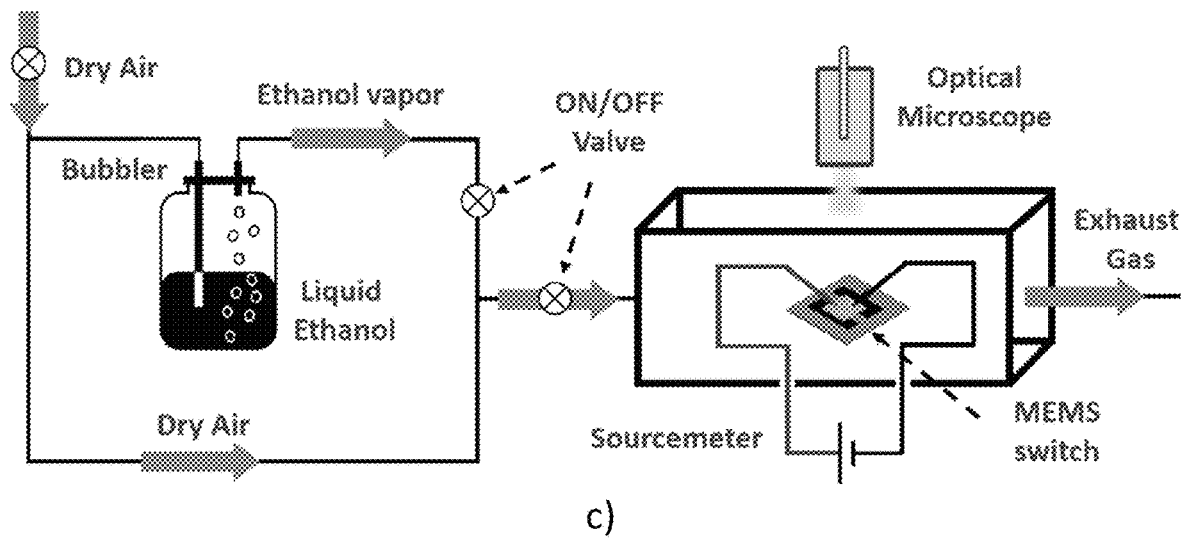
FIG. 6C shows the experimental setup used to expose the prototype VOC sensor to ethanol vapor.
Figure 6D:
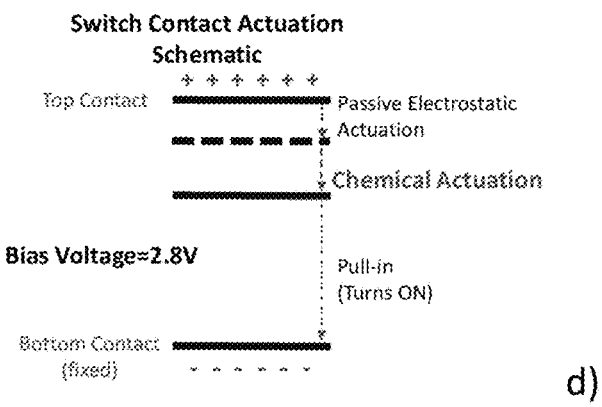
FIG. 6D shows the relative contributions of electrostatic actuation, chemical (VOC-induced) actuation, and bias voltage to contact closure.
Figure 6E:
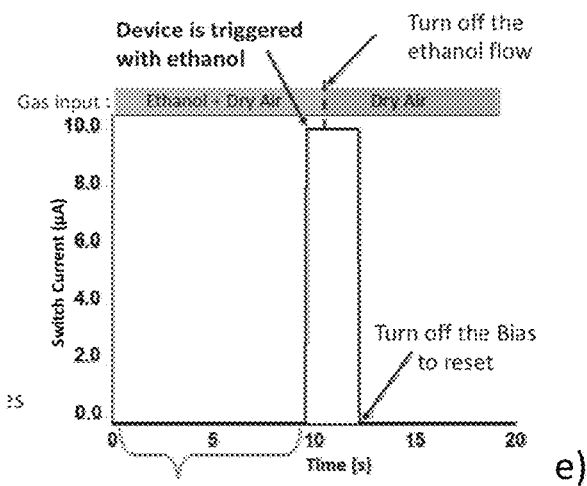
FIG. 6E shows switch current as a function of exposure of the prototype device to ethanol vapor.

FIGS. 6A-6C show schematic representations of a prototype VOC sensor and experimental setup for its testing. The effect of voltage biasing of the switch to improve sensitivity are shown in FIG. 6D. Results obtained with the prototype are shown in FIG. 6E, and are discussed in the Example below.

Figure 7:
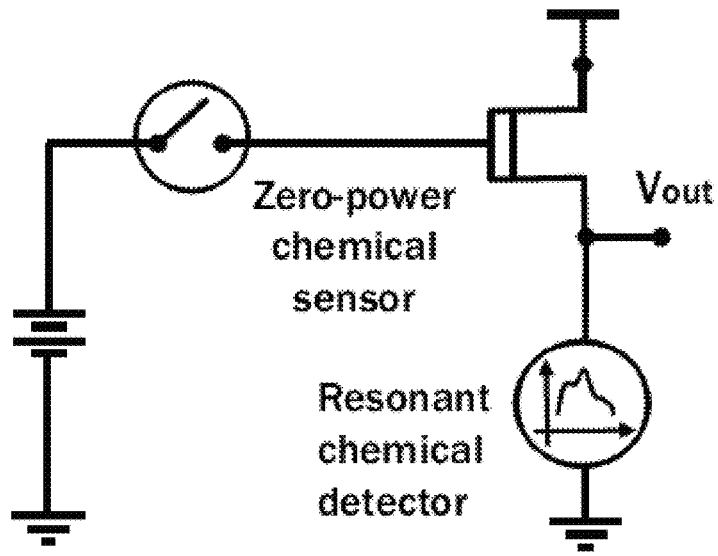
FIG. 7 shows a circuit diagram for a VOC detection system including a zero power VOC sensor that upon VOC detection activates a resonant chemical sensor as well as transmitting a signal to wireless network.
Figure 8:
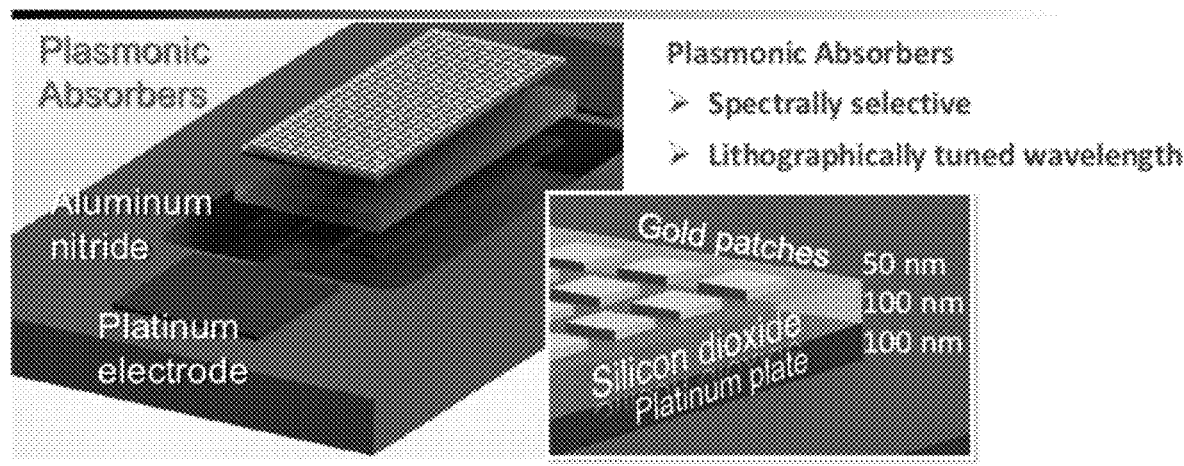
FIG. 8 shows a schematic representation of a resonant infrared detector using a plasmonic absorber (shown in enlarged view).
Figure 9:
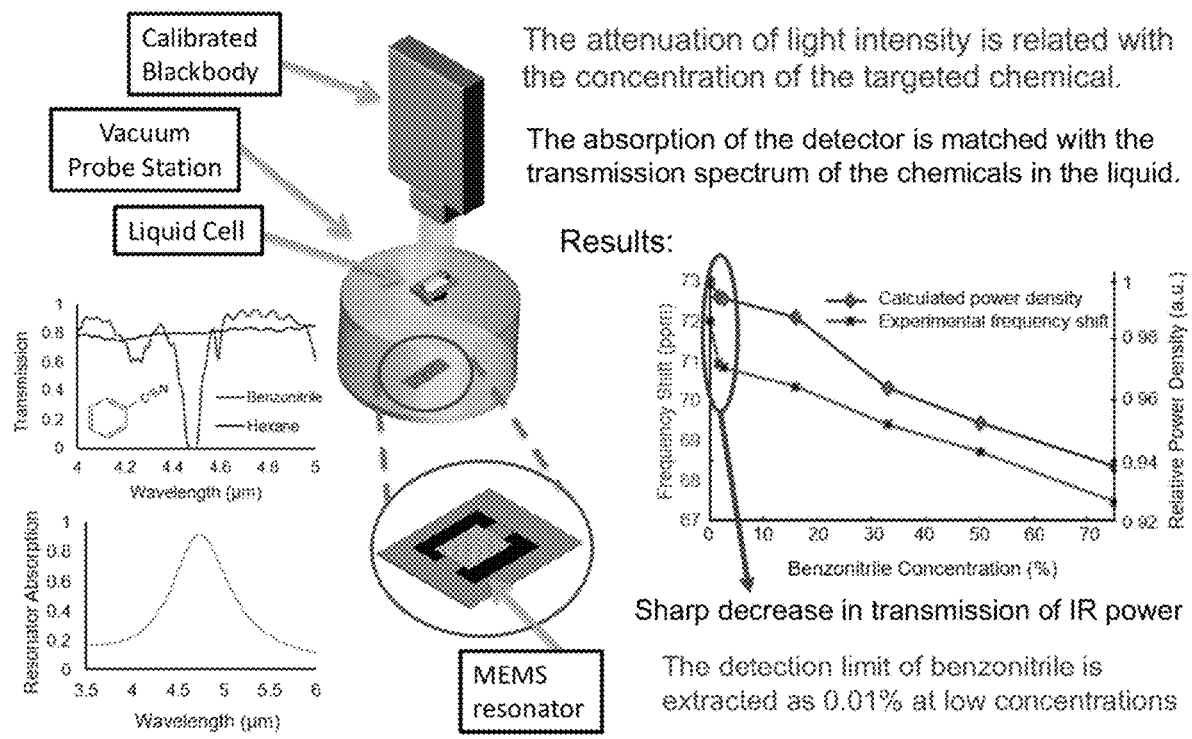
FIG. 9 shows a schematic representation of a spectroscopic infrared chemical detector that uses a MEMS resonator.
Figure 10:
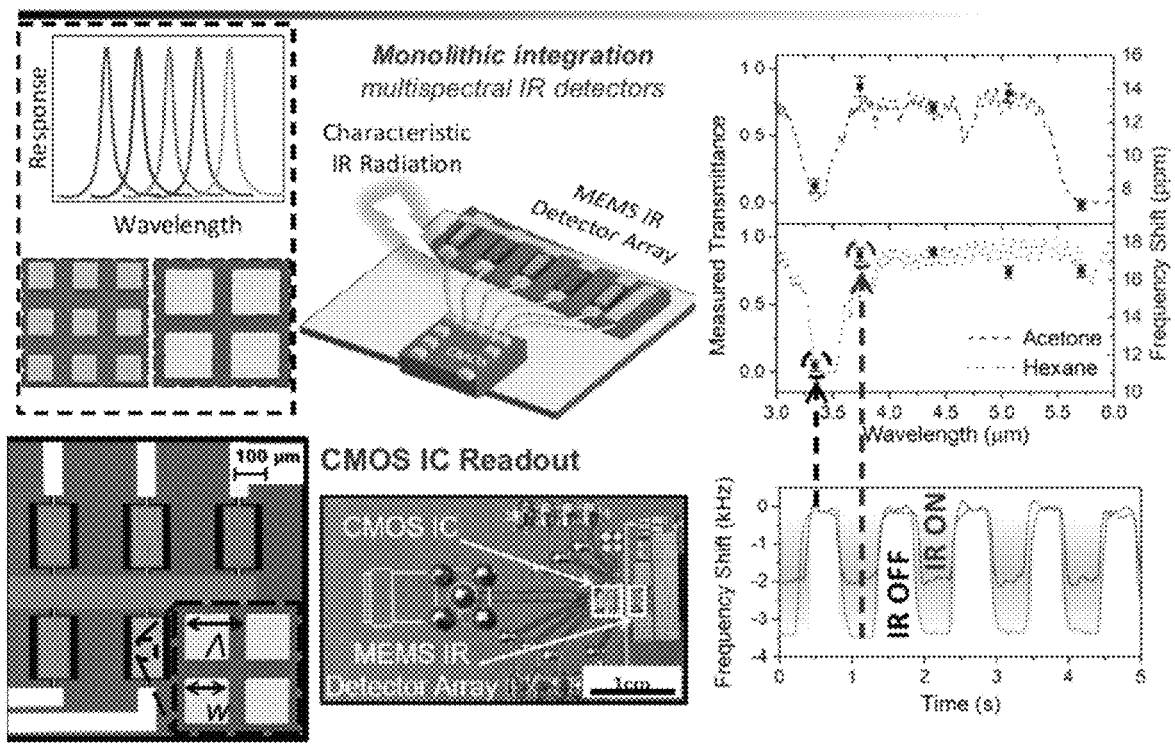
FIG. 10 shows a multispectral infrared chemical sensing system which can be used with or can integrate the zero power VOC sensor of the present technology.

FIG. 7 shows a circuit diagram of a system of the present technology including a VOC sensor and a resonant chemical detector. When the selected VOC is detected, the sensor switch closes the circuit, and the battery can then drive a transmitter and/or an optional resonant chemical detector that performs a more IR spectral analysis for more precise detection of the VOC and elimination of interference from binding of unwanted VOCs to the polymer in the sensor or other spurious effects that may lead to closing of the sensor switch. The structure of a resonant infrared detector that can be used is shown in FIG. 8. Such detectors can be designed to detect selected regions of the IR spectrum, and are described further in WO/2017/082985, which is incorporated herein by reference. FIG. 9 shows a device configuration for use of such MEMS resonators for IR spectral analysis. In FIG. 10 a device is shown for multispectral analysis which can be used for even more precise analysis of VOCs. In this device, two or more resonators are used, with each tuned to a different region of the IR spectrum. A prototype was constructed and tested, and IR spectral differences between acetone and hexane were measured and are shown at the right hand side of the figure.

Example

An experiment was performed using polymethyl-methacrylate (PMMA) as the functional polymer layer and ethanol vapor as the targeted VOC. In order to verify the concept of exploiting VOC-polymer interactions for VOC detection, a chip was fabricated with multiple differently-sized metal-polymer bi-material cantilevers whose schematic is shown in FIG. 6A. For the experiment, the chip was placed in a sealed chamber with liquid ethanol (1 µL) (FIGS. 6B, 6C) and inspection with a microscope was performed after ethanol had fully evaporated. It was observed that the released cantilevers was bent downwards as expected soon after ethanol exposure (FIG. 6E).

The result shows that the aluminum-PMMA beams are highly sensitive to ethanol vapor and clearly demonstrates that the swelling effect can be used for VOC detection by induced micromechanical actuation. Furthermore, it was observed that shorter bi-material beams bend to a smaller extent compared to longer ones. This demonstrates the ability to target different concentration levels of VOCs by changing beam length.

REFERENCES

[1] Grant, O. M., et al. *The Journal of Horticultural Science and Biotechnology* 91.1 (2016): 43-54.
[2] Libelium Smart Agriculture Sensor, Smart Vineyard Lebanon Case Study, www.libelium.com/the-first-smart-vineyard-in-lebanon-chooses-libeliums-technology-to-face-the-climate-change/.
[3] M. N. Hassan, et al. *Plant Biotechnology Journal* 13.6 (2015): 727-739.
[4] R. Fall, et al. *Journal of Geophysical Research: Atmospheres* 104.D13 (1999): 15963-15974.
[5] Z. Qian, et al. "Zero-power infrared digitizers based on plasmonically enhanced micromechanical photoswitches" *Nature Nanotechnology* 12, 969-973, 2017.
[6] K. C. Persaud, *Materials Today* 8.4 (2005): 38-44.
[7] Then, D., A. Vidic, and Ch Ziegler. "A highly sensitive self-oscillating cantilever array for the quantitative and qualitative analysis of organic vapor mixtures." *Sensors and Actuators B: Chemical* 117.1 (2006): 1-9.
[8] Bailer, Marko K., et al. "A cantilever array-based artificial nose." *Ultramicroscopy* 82.1-4 (2000): 1-9.

What is claimed is:

1. A chemical sensor for monitoring a concentration of one or more volatile organic compounds (VOCs) released from a plant under distress from pests or disease, the sensor comprising:
   a first cantilever beam comprising (i) a polymer coating that is exposed to an environment of the sensor and selectively binds to one or more VOCs in said environment, and (ii) a first metal contact disposed at a distal end;
   a second beam isolated from said environment by a barrier material, wherein the second is beam configured either as a cantilevered beam or as a fixed beam, and wherein the second beam comprises a second metal contact disposed at a distal end;
   wherein the first and second metal contacts are separated by a gap when a concentration of said one or more VOCs in said environment is below a selected threshold, and wherein, due to mechanical force in said polymer coating, the first and second metal contacts are in contact when the concentration of said one or more VOCs in said environment are at or above the selected threshold.

2. The sensor of claim 1, wherein the barrier material comprises a metal, a metal oxide, or a polymer.

3. The sensor of claim 1, wherein the contacting of said first and second metal contacts activates a load electronic circuit.

4. The sensor of claim 3, wherein the load electronic circuit comprises a wired or wireless transmitter that transmits a radio frequency signal indicating presence of and/or a level of said one or more VOCs at or above said threshold.

5. The sensor of claim 1, wherein the first beam further comprises a microheater capable of dissociating said one or more VOCs after binding of the one or more VOCs to said polymer coating.

6. The sensor of claim 1, wherein said polymer coating selectively binds one or more VOCs given off by a plant under a condition of disease, stress, or attack by a pathogen or pest.

7. The sensor of claim 1, wherein the polymer coating comprises a polymer selected from the group consisting of polymethyl-methacrylate, polydimethylsiloxane, polyetherurethane, polystyrene, polyurethane, polyvinylpyrrolidone, polypropylene, acetonitrile butadiene styrene, polyacrylate, polycarbonate, polyvinylchloride, polyester, polybutadiene, and polysulfone.

8. The sensor of claim 1, wherein the sensor consumes less than about 10 nW of electric power when the sensor does not detect said one or more VOCs.

9. The sensor of claim 1, wherein said polymer coating selectively binds said one or more VOCs, and wherein said binding results in expansion of said polymer coating.

10. A sensor device for monitoring plants for a disease or pest, the device comprising the sensor of claim 1 and one or more additional sensors selected from the group consisting of sensors detecting and/or quantifying humidity, wind, air flow, air temperature, water temperature, ethylene, a soil mineral, and soil moisture.

11. A sensor device for monitoring plants for a disease or pest, the device comprising the sensor of claim 1 and one or more resonant infrared detectors capable of detecting the same VOC detected by the sensor or a different chemical entity.

12. The sensor device of claim 11, wherein at least one of the one or more resonant infrared detectors is a multispectral infrared detector.

13. A system for monitoring plants for a disease or pest, the system comprising two or more sensors of claim 1 and a networking module capable of receiving sensor data from individual sensors or sensor devices of the system, analyzing the data, and transmitting the data or analyzed data to a remote server for storage and/or analysis.

14. A method for monitoring a concentration of one or more VOCs in an environment, the method comprising:
    (a) providing one or more sensors according to claim 1;
    (b) placing the or more sensors in said environment; and
    (c) detecting a signal from the one or more sensors when a concentration of the one or more VOCs in the environment reaches or exceeds a selected threshold.

15. The method of claim 14, wherein said environment comprises a plant, and wherein detecting the signal is indicative of a disease or pest condition of the plant.

16. The method of claim 14, wherein the VOC is selected from the group of VOCs consisting of air pollutants, flammable gases, corrosive gases, irritative gases, and green leaf volatiles.

17. The method of claim 16, wherein the VOC is an air pollutant, flammable, or corrosive gas selected from the group consisting of toluene, benzene, hexane, cyclohexane, xylene, ethylene dichloride, and butanone.

18. The method of claim 16, wherein the VOC is an irritative gas selected from the group consisting of alcohol, an aliphatic hydrocarbon, ethyl acetate, a glycol ether, methylene chloride, and acetone.

19. The method of claim 16, wherein the VOC is a green leaf volatile selected from the group consisting of aldehydes, esters, hexanol, and hexanal.

20. The method of claim 14, wherein the first beam of the sensor comprises a heater, the method further comprising:
    (d) passing a current through the heater for a first period of time, whereby VOC molecules bound to the polymer are dissipated and the switch is reset into an open configuration; and
    (e) after a second period of time, repeating steps (a)-(c).

* * * * *